United States Patent [19]

Bernardon et al.

[11] Patent Number: 5,705,167
[45] Date of Patent: Jan. 6, 1998

[54] AROMATIC POLYENIC COMPOUNDS AND PHARMACEUTICAL/COSMETIC COMPOSITIONS COMPRISED THEREOF

[75] Inventors: Jean-Michel Bernardon, Le Rouret; Philippe Nedoncelle, Grasse, both of France

[73] Assignee: Centre International de Recherches Dermatologiques Galderma, Valbonne, France

[21] Appl. No.: 429,492

[22] Filed: Apr. 26, 1995

[30] Foreign Application Priority Data

Apr. 26, 1994 [FR] France ................... 94 05017

[51] Int. Cl.$^6$ ................................................. A61K 7/48
[52] U.S. Cl. .............. 424/401; 424/47; 424/701; 424/443; 424/450; 424/451; 424/464; 424/489; 514/844; 514/846; 514/944; 560/62; 560/100; 560/104; 560/106; 560/112; 560/113; 562/490; 562/495; 564/180; 564/182; 568/308; 568/328; 568/425; 568/444; 568/626; 568/716; 568/763; 568/764; 568/780; 585/534
[58] Field of Search .................. 424/401, 464, 424/451, 47, 450, 443, 489, 701; 585/534; 568/308, 328, 425, 444, 626, 716, 763, 764, 780; 560/62, 100, 104, 106, 112, 113; 562/490, 495; 564/180, 182; 514/844, 846, 944

[56] References Cited

U.S. PATENT DOCUMENTS 3,882,157  5/1975  Henrick .................... 260/455 R
4,193,931  3/1980  Loeliger .................... 424/308
4,201,727  5/1980  Chan et al. ................. 568/442

FOREIGN PATENT DOCUMENTS 0486885  5/1992  European Pat. Off. .
2390428  12/1978  France .

OTHER PUBLICATIONS

Journal of Organic Chemistry, vol. 43, No. 26, Dec. 22, 1978, Easton US, pp. 5018–5020, Babu A. patel et al, 'Palladium–Catalyzed Arylation of Conjugated Dienes', p. 5018, line 16–line 17, p. 5018, Table 1, Comp. 3.

*Primary Examiner*—Jyothsan Venkat
*Attorney, Agent, or Firm*—Burns, Doane, Swecker & Mathis, L.L.P.

[57] ABSTRACT

Novel pharmaceutically/cosmetically-active aromatic polyenic compounds have the structural formula (I):

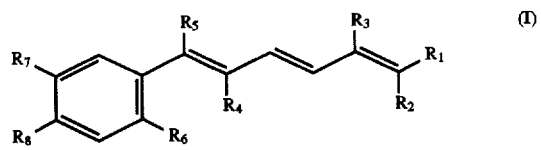

and are useful for the treatment of a wide variety of disease states, whether human or veterinary, for example dermatological, rheumatic, respiratory, cardiovascular, bone and ophthalmological disorders, as well as for the treatment of mammalian skin and hair conditions/disorders.

24 Claims, 2 Drawing Sheets

AROMATIC POLYENIC COMPOUNDS AND PHARMACEUTICAL/COSMETIC COMPOSITIONS COMPRISED THEREOF

CROSS-REFERENCE TO COMPANION APPLICATIONS

Copending applications Ser. No. 08/429,096 pending [Attorney Docket No. 016800-023] and Ser. No. 08/429,045 [Attorney Docket No. 016800-025], both filed concurrently herewith and assigned to the assignee hereof. Cf. copending applications Ser. No. 08/356,913 pending [Attorney Docket No. 016800-006], Ser. No. 08/357,024 pending [Attorney Docket No. 016800-007] and Ser. No. 08/356,680 pending [Attorney Docket No. 016800-008], each filed Dec. 15, 1994 and each also assigned to the assignee hereof.

BACKGROUND OF THE INVENTION

Technical Field of the Invention

The present invention relates to novel aromatic polyenic compounds and to pharmaceutical/cosmetic compositions comprised thereof; the subject compounds are especially useful in human or veterinary medicine, or, alternatively, in cosmetic compositions.

SUMMARY OF THE INVENTION

The compounds according to the invention display a pronounced activity in the fields of cell differentiation and proliferation, and are particularly useful in the topical and systemic treatment of dermatological conditions associated with a keratinization disorder, dermatological (or other) conditions including an inflammatory and/or immunoallergic component, and dermal or epidermal proliferations, whether benign or malignant. The subject compounds can, in addition, be used for the treatment of the degenerative diseases of the connective tissue, for combating aging of the skin, whether photoinduced or chronologic, and for treating cicatrization or healing disorders. They are also useful for ophthalmological applications, especially for the treatment of corneopathies.

The compounds according of this invention are also useful for the treatment of osteoporosis or for the treatment of viral diseases, as well as for the treatment of any disease state associated with hypervitaminosis A. Generally, they are useful for the treatment of any disease or condition associated with a modification in the expression of receptors belonging to the superfamily of steroid and thyroid hormone receptors.

Too, the compounds according to this invention can also be formulated into cosmetic compositions for body and hair care/hygiene.

Briefly, the aromatic polyenic compounds according to the invention have the following structural formula (I):

in which $R_1$ is a —$CH_3$ radical, a radical —$CH_2$—O—$R_9$, a radical —$CH_2$—O—CO—$R_{10}$, or a radical —CO—$R_{11}$, wherein $R_9$, $R_{10}$ and $R_{11}$ are as defined below; $R_2$ is a hydrogen atom or a lower alkyl radical; $R_3$ is a hydrogen atom or a lower alkyl radical; $R_4$ is a hydrogen atom; $R_5$ is a hydrogen atom or a lower alkyl radical; $R_6$ is a hydrogen atom, a linear or branched alkyl radical having from 1 to 20 carbon atoms, a radical —O—$CH_2$—O—$CH_2$—$CH_2$—O—$CH_3$ or a radical —O—$R_{13}$, wherein $R_{13}$ is as defined below; $R_7$ and $R_8$ independently are each (i) a hydrogen atom, (ii) a linear or branched alkyl radical having from 1 to 20 carbon atoms, (iii) a cycloaliphatic radical, (iv) a radical —O—$CH_2$—O—$CH_2$—$CH_2$—O—$CH_3$, (v) a radical —O—$R_{13}$, or (vi) a radical —S(O)$_n R_{13}$, wherein $R_{13}$ and n are as defined below, with the proviso that $R_4$ and $R_6$ may together form, with the carbon atoms from which they depend and with the adjacent benzene ring, a naphthalene ring, and at least one of $R_7$ and $R_8$ has the above definition (ii) or (iii); $R_9$ is a hydrogen atom or a lower alkyl radical; $R_{10}$ is a lower alkyl radical; $R_{11}$ is (a) a hydrogen atom, (b) a lower alkyl radical, (c) a radical of formula:

in which R' and R" independently are each a hydrogen atom, a lower alkyl radical, a mono- or polyhydroxyalkyl radical, an optionally substituted aryl radical, or an amino acid residue or peptide residue or sugar residue, with the proviso that R' and R" may together form, with the nitrogen atom from which they depend, a nitrogen-containing heterocycle, or (d) a radical —$OR_{12}$, wherein $R_{12}$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue, or an amino acid residue or peptide residue; $R_{13}$ is a hydrogen atom or a linear or branched alkyl radical having from 1 to 20 carbon atoms; and n is an integer equal to 0, 1 or 2.

This invention also features the salts of the compounds of formula (I) in the event that the radical $R_1$ represents a carboxylic acid function, or when $R_7$ and/or $R_8$ represents a sulfonic acid function, as well as the optical (chiral) and geometric isomers thereof. When the compounds according to the invention exist in the form of salts, they are preferably alkali metal salts or alkaline earth metal salts, or, alternatively, zinc salts or salts of an organic amine.

DETAILED DESCRIPTION OF BEST MODE AND PREFERRED EMBODIMENTS OF THE INVENTION

More particularly according to the present invention, by the term "lower alkyl radical" is intended an alkyl radical having from 1 to 6 carbon atoms, preferably the methyl, ethyl, isopropyl, butyl, tert-butyl and hexyl radicals.

By the term "linear or branched alkyl radical having from 1 to 20 carbon atoms" is preferably intended methyl, ethyl, propyl, 2-ethylhexyl, octyl, dodecyl, hexadecyl and octadecyl radicals.

By the term "cycloaliphatic radical" is intended a mono- or polycyclic radical such as, for example, the 1-methylcyclohexyl radical or the 1-adamantyl radical.

By the term "monohydroxyalkyl radical" is intended a radical preferably having 2 or 3 carbon atoms, in particular a 2-hydroxyethyl, 2-hydroxypropyl or 3-hydroxypropyl radical.

By the term "polyhydroxyalkyl radical" is intended a radical preferably having from 3 to 6 carbon atoms and from 2 to 5 hydroxyl groups, such as the 2,3-dihydroxypropyl, 2,3,4-trihydroxybutyl and 2,3,4,5-tetrahydroxpentyl radicals, or the pentaerythritol residue.

By the term "aryl radical" is preferably intended a phenyl radical which is optionally substituted by at least one halogen atom, or a hydroxyl or nitro functional group.

By the term "aralkyl radical" is preferably intended a benzyl or phenethyl radical optionally substituted by at least one halogen atom, or a hydroxyl or nitro functional group.

By the term "alkenyl radical" is intended a radical preferably having from 2 to 5 carbon atoms and one or more sites of ethylenic unsaturations, such as, more particularly, the allyl radical.

By the term "sugar residue" is intended a residue derived in particular from glucose, from galactose or from mannose, or alternatively from glucuronic acid.

By the term "amino acid residue" is particularly intended a residue derived from lysine, from glycine or from aspartic acid, and by the term "peptide residue" is more particularly intended a dipeptide or tripeptide residue prepared via the combination of amino acids.

Lastly, by the term "heterocycle" is preferably intended a piperidino, morpholino, pyrrolidino or piperazino radical, optionally substituted in the 4- position by a $C_1$–$C_6$ alkyl radical or a mono- or polyhydroxyalkyl radical as defined above.

Among the compounds of formula (I) according to the present invention, particularly representative are the following:

trans-7-[3-(1-Adamantyl)-4-hydroxyphenyl]-3,7-dimethyl-2,4,6-heptatrienoic acid;

Ethyl trans-7-[3-(1-adamantyl)-4-methoxyphenyl]-3,7-dimethyl-2,4,6-heptatrienoate;

trans-7-[3-(1-Adamantyl)-4-methoxyphenyl]-3,7-dimethyl-2,4,6-heptatrienoic acid;

(2Z,4E,6E)-7-[3-(1-Adamantyl)-4-methoxyphenyl]-3,7-dimethyl-2,4,6-heptatrienoic acid;

trans-5-[-7-(1-Adamantyl)-6-methoxyethoxymethoxy-2-naphthyl]-3-methyl-2,4-pentadienoic acid;

trans-5-[-7-(1-Adamantyl)-6-hydroxy-2-naphthyl]-3-methyl-2,4-pentadienoic acid;

trans-5-[-7-(1-Adamantyl)-6-methoxy-2-naphthyl]-3-methyl-2,4-pentadienoic acid;

trans-5-[-7-(1-Adamantyl)-6-propyloxy-2-naphthyl]-3-methyl-2,4-pentadienoic acid;

trans-7-[3-(1-Methylcyclohexyl)-4-hydroxy-phenyl]-3,7-dimethyl-2,4,6-heptatrienoic acid;

(2Z,4E,6E)-7-[3-(1-Methylcyclohexyl)-4-methoxyphenyl]-3,7-dimethyl-2,4,6-heptatrienoic acid;

trans-7-[3-(1-Adamantyl)-4-isopropyloxyphenyl]-3,7-dimethyl-2,4,6-heptatrienoic acid;

trans-7-[3-(1-Adamantyl)-4-methoxyethoxymethoxyphenyl]-3,7-dimethyl-2,4,6-heptatrienoic acid;

trans-7-[3-(1-Adamantyl)-4-methoxyphenyl]-7-methyl-2,4,6-heptatrienoic acid;

trans-7-[3-(1-Adamantyl)-4-methoxyphenyl]-3,7-dimethyl-2,4,6-heptatrien-1-ol;

trans-7-[3-(1-Adamantyl)-4-methoxyphenyl]-3,7-dimethyl-2,4,6-heptatrien-1-al;

trans-N-Ethyl-7-[3-(1-adamantyl)-4-methoxy-phenyl]-3,7-dimethyl-2,4,6-heptatrienecarboxamide;

trans-N-4-Hydroxyphenyl-7-[3-(1-adamantyl)-4-methoxyphenyl]-3,7-dimethyl-2,4,6-heptatrienecarboxamide;

trans-7-(3-tert-Butyl-4-methoxyethoxymethoxy-phenyl)-3,7-dimethyl-2,4,6-heptatrienoic acid;

Ethyl trans-7-(3-tert-butyl-4-hydroxyphenyl)-3,7-dimethyl-2,4,6-heptatrienoate;

Ethyl trans-7-(3-tert-butyl-4-methoxyphenyl)-3,7-dimethyl-2,4,6-heptatrienoate;

Ethyl trans-7-[4-(1-adamantyl)-3-methoxyphenyl]-3,7-dimethyl-2,4,6-heptatrienoate.

According to the present invention, the more particularly preferred compounds of formula (I) are those in which at least one, and preferably all, of the conditions given below are satisfied:

$R_1$ is a radical —CO—$R_{11}$;

$R_7$ is the adamantyl radical;

$R_4$ is a hydrogen atom;

$R_6$ is a hydrogen atom or a linear or branched alkyl radical having from 1 to 20 carbon atoms; and $R_4$ and $R_6$ together form, with the adjacent benzene ring, a naphthalene ring.

Figure 1:
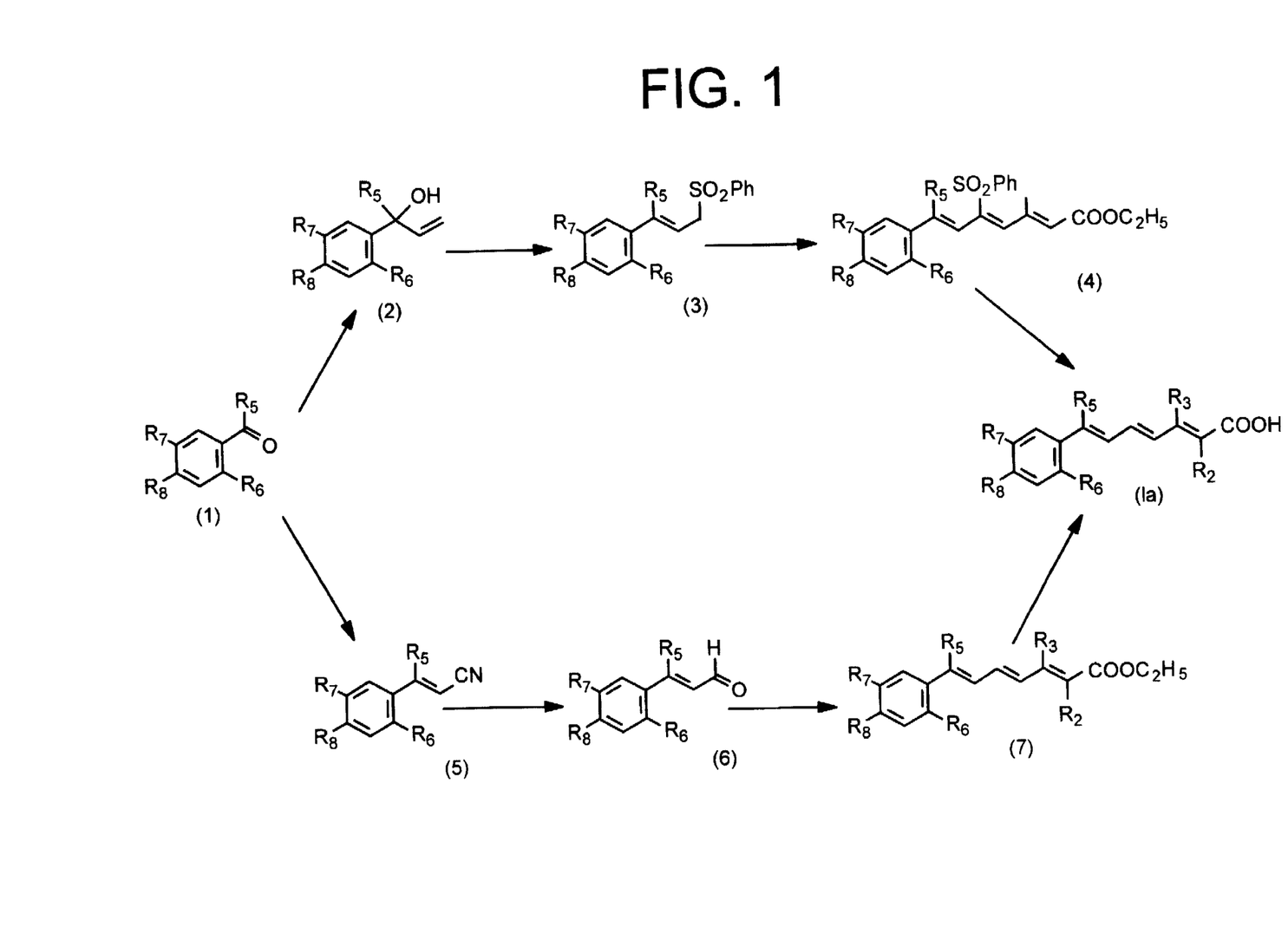
FIGS. 1 and 2 set forth the reaction schemes/mechanisms illustrating representative syntheses for the preparation of the aromatic polyenic compounds according to the present invention.
Figure 2:
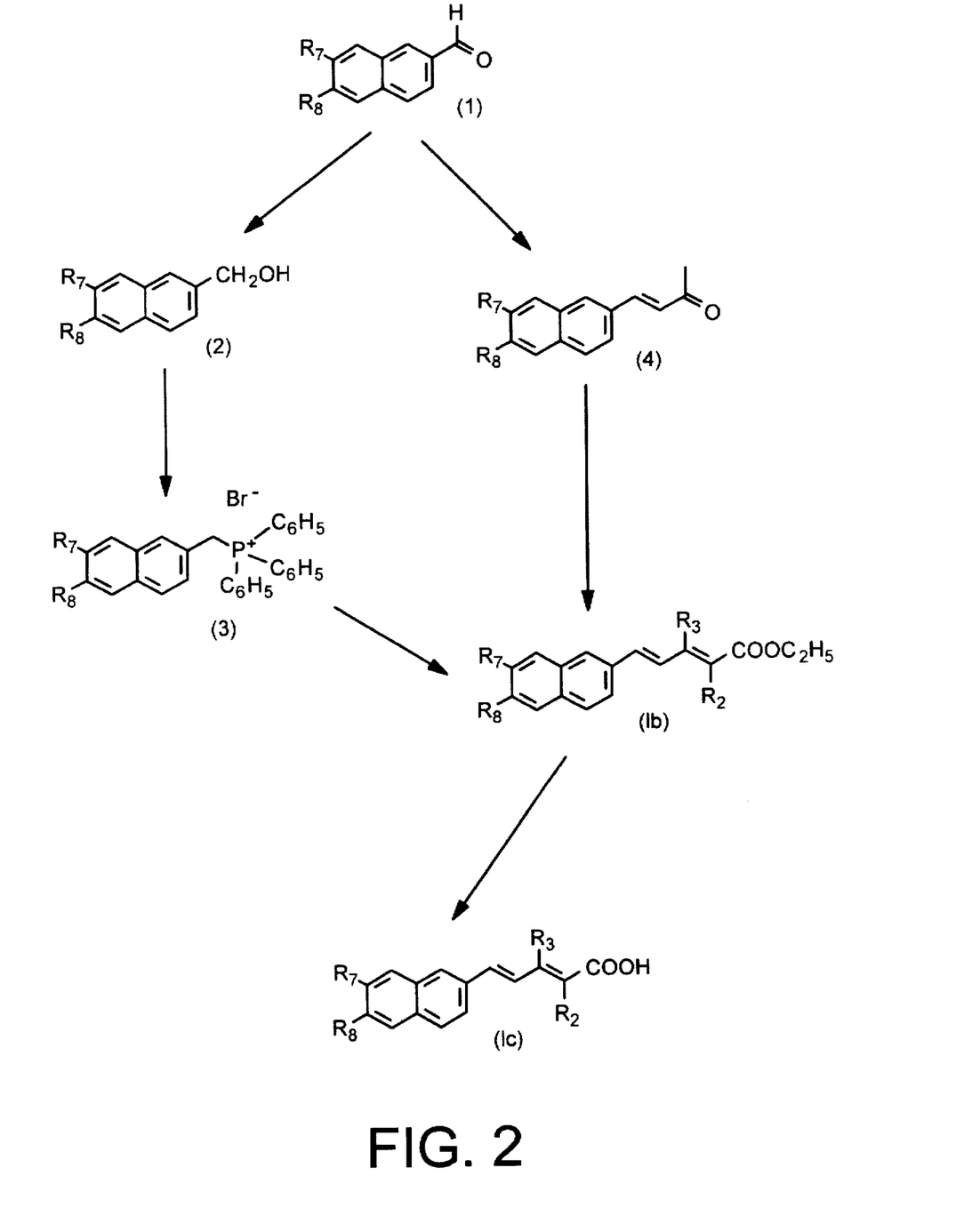

The present invention also features the processes for the preparation of the compounds of formula (I), in particular via the reaction schemes illustrated in FIGS. 1 and 2.

Thus the compounds of formula I(a) may be obtained according to two routes (cf. FIG. 1):

(i) either according to the synthesis described by M. Julia and D. Arnould, in *Bull. Soc. Chim.*, 746 (1973). Hence, by reacting an acetophenone derivative (1) with a vinylmagnesium bromide, the α-hydroxyvinyl (2) is prepared, which is then reacted with sodium phenylsulfinate in order to obtain the compound (3). The anion of the derivative (3) is formed in the presence of a base, for example potassium tert-butoxide, and reacts with an ethyl γ-bromosenecionate to obtain the sulfone ester (4). Removal of the sulfone group is carried out in the presence of a base, for example potassium tert-butoxide or DBU, and, after saponification of the ester function in alcoholic sodium hydroxide or potassium hydroxide, the acid I(a) is ultimately obtained.

(ii) or by reaction of the acetophenone (1), according to a Horner-type reaction, with a C2-phosphononitrile, in order to prepare the propenenitrile derivative (5). After partial reduction with diisobutylaluminium hydride (DIBAH), the propenal derivative (6) is obtained. Treatment of this aldehyde with the lithio derivative of a phosphonate ester results in the formation of the ester (7) which, on saponification in alcoholic sodium hydroxide or potassium hydroxide, ultimately gives the acid I(a).

The compounds of formula I(b) and I(c) may themselves be prepared as follows (cf. FIG. 2):

(i) either from the aldehyde (1) by reduction in the presence of an alkali metal hydride, such as sodium borohydride or lithium aluminum hydride. The alcohol (2) thus obtained is then converted into the phosphonium salt (3) by reaction with $(C_6H_5)_3P.HBr$ in methanol, this compound (3) then being converted into the ester of formula I(b) by the action of the lithio or sodio derivative of a phosphonate ester;

(ii) or from the aldehyde (1) according to a sequence of two Horner-type reactions. First, the compound (1) is reacted with dimethyl 2-oxopropylphosphonate in the presence of DBU in THF to obtain the ketone (4), and the latter is then converted into the ester derivative I(b) by reaction with the lithio or sodio derivative of a phosphonate ester. On saponification of the ester I(b) in the presence of alcoholic sodium hydroxide or potassium hydroxide, the acid I(c) is ultimately obtained.

When $R_6$, $R_7$ and $R_8$ represent the hydroxyl radical, the compounds of formula (I) are advantageously prepared by protecting the phenol function, preferably in the tert-butyldimethylsilyloxy or methoxyethoxymethoxy form, the deprotection then being carried out either in the presence of tetrabutyl-ammonium fluoride or trimethylsilyl iodide, or in acidic medium (HCl).

The present invention also features therapeutic/pharmaceutical applications of the compounds of formula (I).

These compounds exhibit antagonistic activity with respect to the expression of one or more biological labels (markers) in the test for differentiation of mouse embryonic teratocarcinoma cells (F9) (*Skin Pharmacol.*, 3, pp. 256–267 (1990) and/or for the differentiation of human keratinocytes in vitro (*Anal. Biochem.*, 192, pp. 232–236 (1991)). They may also exhibit a specific agonistic activity with respect to certain receptors, and antagonistic activities with respect to others.

The compounds according to the invention are particularly suitable in the following fields of thearapy:

(1) for treating dermatological conditions associated with a keratinization disorder related to differentiation and proliferation, in particular for treating simple acne, comedones, polymorphonuclear leucocytes, rosacea, nodulocystic acne, severe cystic acne, senile acne and secondary acnes such as solar, medication-related or occupational acne, (2) for treating other types of keratinization disorders, in particular ichthyosis, ichthyosiform states, Darier's disease, palmoplantar keratoderma, leucoplasias and leucoplasiform states, and cutaneous or mucous (buccal) lichen, (3) for treating other dermatological conditions associated with a keratinization disorder manifesting an inflammatory and/or immunoallergic component and, in particular, all forms of psoriasis, whether cutaneous, mucous or ungual, and even psoriatic rheumatism, or alternatively cutaneous atopy, such as eczema or respiratory atopy or alternatively gingival hypertrophy; the compounds may also be used for treating inflammatory conditions not exhibiting keratinization disorder, (4) for treating all dermal or epidermal proliferations, whether benign or malignant, and whether or not of viral origin or otherwise, such as common warts, flat warts and verruciform epidermodysplasia, oral or florid papillomatoses and the proliferations which can be induced by ultraviolet radiation, in particular in the case of basocellular and spinocellular epithelioma, (5) for treating other dermatological disorders, such as bullosis and collagen diseases, (6) for treating certain ophthalmological disorders, especially corneopathies, (7) for repairing or combating aging of the skin, whether photoinduced or chronologic, or for reducing actinic keratoses and pigmentations, or any pathologies associated with chronological or actinic aging, (8) for preventing or curing the stigmata of epidermal and/or dermal atrophy induced by local or systemic corticosteroids, or any other form of cutaneous atrophy, (9) for preventing or treating cicatrization or healing disorders or for preventing or repairing vibices and stretch marks, (10) for combating disorders of sebaceous functioning, such as the hyperseborrhoea of acne or simple seborrhoea, (11) for the treatment or prevention of cancerous or precancerous states, (12) for the treatment of inflammatory conditions such as arthritis, (13) for the treatment of any skin or general disease state of viral origin, (14) for the prevention or treatment of alopecia, (15) for the treatment of dermatological or general conditions including an immunological component, (16) for the treatment of ailments of the cardiovascular system, such as arteriosclerosis, (17) for the treatment or prevention of osteoporosis.

For the aforesaid therapeutic or pharmaceutical applications, the compounds according to the invention may advantageously be used in combination with other bioactive compounds, for example with the D vitamins or derivatives thereof, with corticosteroids, with anti-free-radical agents, with α-hydroxy or α-keto acids or derivatives thereof, or alternatively with ion-channel blockers. By the term "D vitamins or derivatives thereof" are intended, for example, derivatives of vitamin $D_2$ or $D_3$ and in particular 1,25-dihydroxyvitamin $D_3$. By the term "anti-free-radical agents" are intended, for example, α-tocopherol, superoxide dismutase, ubiquinol or certain metal-chelating agents. By the term "α-hydroxy or α-keto acids or derivatives thereof" are intended, for example, lactic acid, malic acid, citric acid, glycolic acid, mandelic acid, tartaric acid, glyceric acid or ascorbic acid or the salts, amides or esters thereof. By the term "on-channel blockers" are intended, for example, Minoxidil (2,4-diamino-6-piperidinopyrimidine 3-oxide) and derivatives thereof.

The present invention thus also features medicinal compositions containing at least one compound of formula (I), one of the optical or geometric isomers thereof, or one of the salts or other derivatives thereof.

The pharmaceutical/therapeutic compositions of the present invention, intended in particular for the treatment of the aforesaid disease states comprise a pharmaceutically acceptable vehicle, carrier or diluent which is compatible with the mode or regime of administration selected for the given composition, at least one compound of formula (I), one of the optical or geometrical isomers thereof, or one of the salts, etc., thereof.

The compounds according to the invention may be administered via the systemic, enteral, parenteral, topical or ocular route.

Via the enteral route, the medicinal/pharmaceutical compositions may be in the form of tablets, gelatin capsules, dragees, syrups, suspensions, solutions, elixirs, powders, granules, emulsions, microspheres or nanospheres or lipidic or polymeric vesicles which permit controlled release. Via the parenteral route, the compositions may be in the form of solutions or suspensions for infusion or for injection.

The compounds according to the invention are generally administered at a daily dose of approximately 0.01 mg/kg to 100 mg/kg of body weight, and this at the rate or regime of in 1 to 3 doses per diem.

Via the topical route, the pharmaceutical compositions based on compounds according to the invention are more particularly intended for the treatment of the skin and the mucosae and may then be in the form of pasty ointments, creams, milks, creamy ointments, powders, impregnated pads, solutions, gels, sprays, lotions or suspensions. They may also be in the form of microspheres or nanospheres or lipidic or polymeric vesicles or polymeric patches and hydrogels which permit controlled release. These topical-route compositions may furthermore be either in anhydrous form or in an aqueous form, depending on the particular clinical indication. Via the ocular route, they are principally eye drops.

These compositions for topical or ocular application contain at least one compound of formula (I), or one of the optical or geometrical isomers thereof, or, alternatively, one of the salts, etc., thereof, at a concentration preferably ranging from 0.001% to 5% by weight relative to the total weight of the composition.

The compounds of formula (I) according to the invention also find application in the cosmetic field, in particular for body and hair care/hygiene, and especially for treating skin-types with a tendency towards acne, for promoting the regrowth of the hair, for combating hair loss, for controlling the greasy appearance of the skin or of the hair, for protection against the deleterious effects of the sun or for the treatment of physiologically dry skin-types, and for preventing and/or combating photoinduced or chronologic aging.

For cosmetic applications, the compounds according to the invention may, furthermore, be advantageously employed in combination with other compounds displaying retinoid-type activity, with the D vitamins or derivatives thereof, with corticosteroids, with anti-free-radical agents, with α-hydroxy or α-keto acids or derivatives thereof, or, alternatively, with ion-channel blockers, all of these various active agents being as defined above.

The present invention therefore also features cosmetic compositions comprising a cosmetically acceptable vehicle, carrier or diluent suitable for topical application, at least one compound of formula (I), or one of the optical or geometrical isomers thereof or one of the salts thereof, etc. Such cosmetic compositions are advantageously in the form of a cream, a milk, a lotion, a gel, lipidic or polymeric microspheres or nanospheres or vesicles, a soap or a shampoo.

The concentration of the compound of formula (I) in the cosmetic compositions according to the invention advantageously ranges from 0.001% to 3% by weight relative to the total weight of the composition.

The medicinal and cosmetic compositions according to the invention may additionally contain inert additives or even pharmacodynamically or cosmetically active additives or combinations of these additives, and especially: wetting agents; depigmenting agents such as hydroquinone, azelaic acid, caffeic acid or kojic acid; emollients; hydrating or moisturizing agents such as glycerol, PEG 400, thiamorpholine and derivatives thereof or alternatively urea; anti-seborrhoeic agents or anti-acne agents such as S-carboxymethylcysteine and S-benzylcysteamine and the salts or derivatives thereof, or benzoyl peroxide; antibiotics such as erythromycin and the esters thereof, neomycin, clindamycin and the esters thereof, and tetracyclines; antifungal agents such as ketoconazole or 4,5-polymethylene-3-isothiazolidones; agents promoting the regrowth of the hair, such as Minoxidil (2,4-diamino-6-piperidinopyrimidine 3-oxide) and derivatives thereof, diazoxide (7-chloro-3-methyl-1,2,4-benzothiadiazine 1,1-dioxide) and phenytoin (5,5-diphenylimidazolidine-2,4-dione); non-steroidal anti-inflammatory agents; carotenoids and, in particular, β-carotene; anti-psoriatic agents such as anthraline and derivatives thereof; and, lastly, eicosa-5,8,11,14-tetraynoic acid and eicosa-5,8,11-triynoic acid, and the esters and amides thereof.

The compositions according to the invention may also contain flavor-enhancing agents, preservatives such as para-hydroxybenzoic acid esters, stabilizing agents, moisture regulators, pH regulators, osmotic pressure modifiers, emulsifying agents, UV-A and UV-B screening agents, and antioxidants such as α-tocopherol, butylhydroxyanisole or butylhydroxytoluene.

In order to further illustrate the present invention and the advantages thereof, the following specific examples are given, it being understood that same are intended only as illustrative and in nowise limitative.

EXAMPLE 1

Preparation of trans-7-[3-(1-adamantyl)-4-hydroxypylhen]-3,7-dimethyl-2,4,6-heptatrienoic acid (a) Syntheses of 2-[3-(1-adamantyl)-4-tert-butyldimethylsilyloxy-phenyl]-3-buten-2-ol:

385 mg (1 mmol) of 3-(1-adamantyl)-4-tert-butyldimethylsilyloxyacetophenone and 20 ml of THF were introduced into a three-necked flask, followed by dropwise addition of 1.1 ml (1.1 mmol) of vinyl-magnesium bromide solution (1M) such that the temperature of the reaction medium did not exceed 20° C. The mixture was then stirred at room temperature for one hour and the reaction medium was poured into an ice/water mixture and extracted with ethyl ether, and the organic phase was separated out after settling of the phases had occurred, dried over magnesium sulfate and evaporated.

The residue obtained was purified by chromatography on a column of silica eluted with a mixture of ethyl ether and hexane (15/85). 380 mg of the expected alcohol were thus collected (yield: 92%) in the form of an oil.

(b) Synthesis of 3-[3-(1-adamantyl)-4-tert-butyldimethylsilyloxy-phenyl]-2-butenesulfonylbenzene:

5.9 g (35.8 mmol) of sodium benzenesulfinate, 8 ml of water and 12 ml of acetic acid were introduced into a round-bottomed flask. The mixture was heated to 60° C. and 7.37 g (17.8 mmol) of the alcohol derivative obtained above were then added over 15 minutes, and this temperature was maintained for four hours. The reaction medium thus obtained was poured into water and extracted with hexane, and the organic phase was separated out after settling of the phases had taken place, washed with water, dried over magnesium sulfate and evaporated.

The residue obtained was purified by chromatography on a column of silica eluted with a mixture of ethyl acetate and hexane (10/90). After evaporation of the solvents, 3.1 g of the expected compound were collected (yield: 32%).

(c) Synthesis of ethyl trans-7-[3-(1-adamantyl)-4-tert-butyldimethylsilyloxyphenyl]-5-benzenesulfonyl-3,7-dimethyl-2,6-heptadienoate:

765 mg (6.8 mmol) of potassium tert-butoxide and 5 ml of a solution comprising a mixture of THF and N-methylpyrrolidine (5:1) wee introduced into a round-bottomed flask. While cooling the mixture thus obtained to −65° C. there wee added, successively and dropwise, firstly a first solution consisting of 3 g (5.68 mmol) of the derivative obtained in step (b) diluted in 2.5 ml of a [THF/N-methylpyrrolidine] mixture which was identical to that indicated above, followed by a second solution of 1.3 g (6.25 mmol) of ethyl γ-bromosenecionate diluted in 1 ml of THF and the entire contents were stirred for one hour at −65° C.

25 ml of ethyl ether were then added, the temperature permitted to increase to 0° C., 35 ml of water were added and the mixture was extracted with ethyl ether. The organic phase was separated out after settling of the phases had taken place, dried over magnesium sulfate and then evaporated.

The residue obtained was purified by chromatography on a column of silica eluted with a mixture of ethyl acetate and hexane (15/85). After evaporation, 4 g of the expected ester were collected (yield: 100%) in the form of a colorless oil.

(d) Synthesis of ethyl trans-7-[3-(1-adamantyl)-4-hydroxyphenyl]-3,7-dimethyl-2,4,6-heptatrienoate:

4 g (6.25 mmol) of the above ester obtained in step (c) and 40 ml of THF were introduced into a round-bottomed flask under a stream of nitrogen, the mixture was cooled to −30° C. and 700 mg (6.25 mmol) of potassium tert-butoxide were added. The mixture was stirred at this same temperature for one hour, the temperature was permitted to increase to room temperature, and the reaction medium was neutralized and extracted with ethyl ether. The organic phase was separated out after settling of the phases had taken place, dried over magnesium sulfate and evaporated.

The residue obtained was purified by chromatography on a column of silica eluted with a mixture of ethyl acetate and hexane (20/80). After evaporation of the solvents, 863 mg of ethyl 7-[3-(1-adamantyl)-4-hydroxyphenyl]-3,7-dimethyl-2,4,6-heptatrienoate were collected (yield: 34%) in the form of an oil.

(e) Synthesis of trans-7-[3-(1-adamantyl)-4-hydroxyphenyl]-3,7-dimethyl -2,4,6-heptatrienoic acid:

813 mg (2 mmol) of the ester obtained in step (d) above and 50 ml of methanol were introduced into a round-bottomed flask sheltered from the light and under a stream of nitrogen. 2.5 ml (10 mmol) of sodium hydroxide (4N) were added dropwise and the mixture was heated to reflux for two hours. After cooling, ethyl acetate was added and the mixture was acidified with hydrochloric acid (4N), and the organic phase was separated out after settling of the phases had taken place, washed with water, dried over magnesium sulfate and evaporated.

The residue obtained was purified by chromatography on a column of silica eluted with a mixture of THF and hexane (30/70). After evaporation of the solvents, 400 mg of 7-[3-(1-adamantyl)-4-hydroxyphenyl]-3,7-dimethyl-2,4,6-heptatrienoic acid, with a melting point of 210° C. with decomposition, were collected (yield: 53%).

EXAMPLE 2

Preparation of ethyl trans-7-[3-(1-adamantyl)-4-methoxyphenyl]-3,7-dimethyl-2,4,6-heptatrienoate 813 mg (2 mmol) of the ester obtained in Example 1(d) and 30 ml of THF were introduced not actually applied). Into a round-bottomed flask under a stream of nitrogen. 60 mg (2 mmol) of sodium hydride (80% in oil) were added portionwise and the mixture was stirred until the evolution of gas ceased. 125 µl (2 mmol) of methyl iodide were then added and the mixture was stirred at room temperature for three hours. The reaction medium was poured into water and extracted with ethyl ether, and the organic phase was separated out after settling of the phases had taken place, dried over magnesium sulfate and evaporated.

The residue obtained was purified on a column of silica eluted with a mixture of dichloromethane and hexane (50/50). 714 mg of the expected ester were collected (yield: 85%) in the form of an oil.

EXAMPLE 3

Preparation of trans-7-[3-(1-adamantyl)-4-methoxyphenyl]-3,7-dimethyl-2,4,6-heptatrienoic acid (a) Synthesis of 2-[3-(1-adamantyl)-4-methoxyphenyl]-3-buten-2-ol:

In a manner similar to that of Example 1(a), starting with 12.7 g (44.6 mmol) of 3-(1-adamantyl)-4-methoxyacetophenone and after chromatography on a column of silica eluted with a mixture of ethyl acetate and hexane (10/90), 7.6 g of the expected alcohol were obtained (yield: 54%) in the form of a yellow oil.

(b) Synthesis of 3-[3-(1-adamantyl)-4-methoxyphenyl]-2-butene-sulfonylbenzene:

In a manner similar to that of Example 1(b), starting with 7.6 g (24.2 mmol) of the alcohol obtained in step (a) above and after chromatography on a column of silica eluted with a mixture of ethyl acetate and hexane (15/85), 5.2 g of the expected compound were obtained (yield: 49%).

(c) Synthesis of ethyl trans-7-[3-(1-adamantyl)-4-methoxyphenyl]-5-benzenesulfonyl-3,7-dimethyl-2,6-heptadienoate:

In a manner similar to that of Example 1(c), starting with 5.18 g (11.9 mmol) of 3-[3-(1-adamantyl)-4-methoxyphenyl]-2-butenesulfonylbenzene obtained in step (b) above and after chromatography on a column of silica eluted with a mixture of ethyl acetate and hexane (20/80), 5 g (75%) of the expected ester were obtained.

(d) Synthesis of trans-7-[3-(1-adamantyl)-4-methoxyphenyl]-3,7-dimethyl-2,4,6-heptatrienoic acid:

4.6 g (8.2 mmol) of the ester prepared in step (c) above and 50 ml of methanol wee introduced into a round-bottomed flask sheltered from the light and under a stream of nitrogen. 23 ml (98 mmol) of methanolic potassium hydroxide (4N) wee then added dropwise and the mixture was heated to reflux for two hours. After cooling, ethyl ether and water were added and the mixture was acidified with sulfuric acid (4N), and the organic phase was separated out after settling of the phases had taken place, washed with water, dried over magnesium sulfate and evaporated.

The residue obtained was purified by chromatography on a column of silica eluted with a mixture of ethyl acetate and dichloromethane (15/85). After evaporation of the solvents, 2.3 g of trans-7-[3-(1-adamantyl)-4-methoxyphenyl]-3,7-dimethyl-2,4,6-heptatrienoic acid, with a melting point of 212° C. with decomposition, were collected (yield: 72%).

EXAMPLE 4

Preparation of (2Z,4E,6E)-7-[3-(1-adamantyl)-4-methoxyphenyl]-3,7-dimethyl-2,4,6-heptatrienoic acid In the reaction of Example 3 (d), during the chromatography on silica eluted with a mixture of ethyl acetate and dichloromethane (15/85), 310 mg of (2Z,4E,6E)-7-[3-(1-adamantyl)-4-methoxyphenyl]-3,7-dimethyl-2,4,6-heptatrienoic acid, with a melting point of 207° C. with decomposition, were also obtained (yield: 9%).

EXAMPLE 5

Preparation of trans-5-[7-(1-adamantyl)-6-methoxyethoxy -methoxy-2-naphthyl]-3-methyl-2,4-pentadienoic acid (a) Synthesis of 7-(1-adamantyl)-6-hydroxy-2-bromonaphthalene:

22.3 g (0.1 mol) of 6-bromo-2-naphthol, 15.2 g (0.1 mol) of 1-adamantanol and 100 ml of dichloromethane were introduced into a round-bottomed flask. 5.5 ml of concentrated hydrochloric acid were added and the mixture was stirred at room temperature for twelve hours. The mixture was evaporated to dryness and the residue was taken up in water and neutralized with sodium bicarbonate. The resulting mixture was extracted with ethyl acetate and the organic phase was separated out after settling of the phases had taken place, dried over magnesium sulfate and evaporated.

The residue obtained was triturated in a mixture of dichloromethane and heptane (30/70), filtered and dried. 19 g (53%) of the expected compound, with a melting point of 215–6° C., were collected.

(b) Synthesis of 7-(1-adamantyl)-6-methoxyethoxy-2-bromonaphthalene:

17.85 g (50 mmol) of 7-(1-adamantyl)-6-hydroxy-2-bromonaphthalene and 200 ml of DMF were introduced into a three-necked flask under a stream of nitrogen. 1.8 g (60 mmol) of sodium hydride (80% in oil) were introduced portionwise and the mixture was stirred at room temperature until the evolution of gas ceased. The mixture was cooled to 5° C. and 6.9 ml (60 mmol) of methoxyethoxymethyl chloride were introduced dropwise, and was stirred for two hours. The reaction medium was poured into ice-water and extracted with ethyl ether, and the organic phase was separated out after settling of the phases had taken place, dried over magnesium sulfate and evaporated.

The residue obtained was purified by chromatography on a column of silica eluted with a mixture of dichloromethane and heptane (40/60). After evaporation of the solvents, 19.5 g (87%) of the expected compound, with a melting point of 99°–100° C., were collected.

(c) Synthesis of 7-(1-adamantyl)-6-methoxyethoxymethoxy-2-naphthalenecarboxaldehyde:

15 g (33.7 mmol) of 7-(1-adamantyl)-6-methoxyethoxymethoxy-2-bromonaphthalene and 150 ml of THF were introduced into a three-necked flask under a stream of nitrogen. A solution of 14.9 ml of n-butyllithium (2.5M in hexane) was added dropwise at –78° C. and the mixture was stirred for one hour. At this same temperature, 3.1 ml (40.4 mmol) of DMF were added and the mixture was permitted to return to room temperature. The reaction medium was poured into saturated aqueous ammonium chloride solution and extracted with ethyl ether, and the organic phase was separated out after settling of the phases had taken place, dried over magnesium sulfate and evaporated.

The residue obtained was purified by chromatography on a column of silica eluted with a mixture of ethyl acetate and heptane (1/4). After evaporation of the solvents, 7.7 g (57%) of the expected aldehyde derivative, with a melting point of 115°–6° C., were collected.

(d) Synthesis of ethyl trans-5-[-7-(1-adamantyl)-6-methoxyetyoxy-methoxy-2-naphthyl]-3-methyl-2,4-pentadienoate:

3.1 ml (22.2 mol) of diisopropylamine, 40 ml of HMPA and 60 ml of THF were introduced into a three-necked flask under a stream of nitrogen. 8.9 ml of n-butyllithium (2.5M in hexane) were introduced dropwise at 0° C. and the mixture was stirred for 30 min. A solution of 6.3 ml (20.7 mmol) of triethyl 3-methyl-4-phosphonocrotonate in 50 ml of THF was added dropwise at –60° C., and the mixture was stirred for one hour, followed by dropwise addition of a solution of 6 g (14.8 mmol) of 7-(1-adamantyl)-6-methoxyethoxymethoxy-2-naphthalenecarboxaldehyde dissolved in 30 ml of THF, and the mixture was permitted to return to room temperature. The reaction medium was poured into saturated aqueous ammonium chloride solution and extracted with ethyl ether, and the organic phase was separated out after settling of the phases had taken place, dried over magnesium sulfate and evaporated.

The residue obtained was purified by chromatography on a column of silica eluted with a mixture of ethyl acetate and heptane (1/9). After evaporation of the solvents, 6 g (85%) of the expected ethyl ester were collected in the form of a yellow oil.

(e) Synthesis of trans-5-[-7-(1-adamantyl)-6-methoxyethoxymethoxy-2-naphthyl]-3-methyl-2,4-pentadienoic acid:

In a manner similar to that of Example 1(e), starting with 1.2 g (2.5 mmol) of the above ethyl ester, 350 mg (35%) of trans-5-[-7-(1-adamantyl)-6-methoxyethoxymethoxy-2-naphthyl]-3-methyl-2,4-pentadienoic acid, with a melting point of 195°–6° C., were obtained.

EXAMPLE 6

Preparation of trans-5-[-7-(1-adamantyl)-6-hydroxy-2-naphthyl]-3-methyl-2,4-pentadienoic acid (a) Synthesis of ethyl trans-5-[-7-(1-adamantyl)-6-hydroxy-2-naphthyl]-3-methyl-2,4-pentadienoate:

5.6 g (11.8 mmol) of ethyl trans-5-[-7-(1-adamantyl)-6-methoxyethoxymethoxy-2-naphthyl]-3-methyl-2,4-pentadienoate and 60 ml of dichloromethane were introduced into a three-necked flask under a stream of nitrogen. 13 ml of boron trichloride (1M in dichloromethane) were added dropwise at –70° C. and the mixture was permitted to return to room temperature. The reaction medium was poured into ice-water and extracted with ethyl ether, and the organic phase was separated out after settling of the phases had taken place, dried over magnesium sulfate and evaporated.

The residue obtained was purified by chromatography on a column of silica eluted with a mixture of ethyl acetate and heptane (1/4). After evaporation of the solvents, 1.4 g (85%) of the expected ethyl ester, with a melting point of 212°–4° C., were collected.

(b) Synthesis of trans-5-[-7-(1-adamantyl)-6-hydroxy-2-naphthyl]-3-methyl-2,4-pentadienoic acid:

In a manner similar to that of Example 1(e), starting with 1.3 g (3.1 mmol) of the above ethyl ester, 320 mg (25%) of trans-5-[-7-(1-adamantyl)-6-hydroxy-2-naphthyl]-3-methyl-2,4-pentadienoic acid, with a melting point of 240°–5° C., were obtained.

EXAMPLE 7

Preparation of trans-5-[-7-(1-adamantyl)-6-methoxy-2-naphthyl]-3-methyl-2,4-pentadienoic acid (a) Synthesis of ethyl trans-5-[-7-(1-adamantyl)-6-methoxy-2-naphthyl]-3-methyl-2,4-pentadienoate:

In a manner similar to that of Example 2, by reaction of 1.4 g (3.3 mmol) of ethyl trans-5-[-7-(1-adamantyl)-6-hydroxy-2-naphthyl]-3-methyl-2,4-pentadienoate with 260 μl (4 mmol) of methyl iodide, 330 mg (80%) of the expected ethyl ester were obtained.

(b) Synthesis of trans-5-[-7-(1-adamantyl)-6-methoxy-2-naphthyl]3-methyl-2,4-pentadienoic acid:

In a manner similar to that of Example 1(e), starting with 1.1 g (2.7 mmol) of the above ethyl ester, 478 mg (43%) of trans-5-[-7-(1-adamantyl)-6-methoxy-2-naphthyl]-3-methyl-2,4-pentadienoic acid, with a melting point of 290°–1° C., were obtained.

EXAMPLE 8

Preparation of trans-5-[7-(1-adamantyl)-6-propyloxy-2-nahpthyl]-3-methyl-2,4-pentadienoic acid (a) Synthesis of ethyl trans-5-[-7-(1-adamantyl)-6-proploxy-2-naphthyl]-3-methyl-2,4-pentadienoate:

In a manner similar to that of Example 2, by reaction of 1.4 g (3.3 mmol) of ethyl trans-5-[-7-(1-adamantyl)-6-hydroxy-2-naphthyl]-3-methyl-2,4-pentadienoate with 400 μl (4 mmol) of 3-iodopropane, 1.12 g (75%) of the expected ethyl ester, with a melting point of 133°–4° C., were obtained.

(b) Synthesis of trans-5-[-7-(1-adamantyl)-6-proploxy-2-naphthyl]-3-methyl-2,4-pentadienoic acid:

In a manner similar to that of Example 1(e), starting with 1.1 g (2.4 mmol) of the above ethyl ester, 770 mg (80%) of trans-5-[-7-(1-adamantyl)-6-propyloxy-2-naphthyl]-3-methyl-2,4-pentadienoic acid, with a melting point of 240°–1° C., were obtained.

EXAMPLE 9

Preparation of trans-7-[3-(1-methylcyclohexyl)-4-hydroxy-phenyl]-3,7-dimethyl-2,4,6-heptatrienoic acid (a) Synthesis of 3-(1-methylcyclohexyl)-4-methoxyphenylethanone:

4.6 g (1.85 mmol) of 3-(1-methylcyclohexyl)-4-methoxybenzoic acid and 50 ml of THF were introduced into a three-necked flask under a stream of nitrogen. 29 ml (4.6 mmol) of methyllithium (1.6M in ethyl ether) were added dropwise at –30° C. and the mixture was permitted to return to room temperature. The reaction medium was poured into ice-water and extracted with ethyl acetate, and the organic phase was separated out after settling of the phases had taken place, dried over magnesium sulfate and evaporated.

4.6 g (99%) of the expected ketone derivative were collected in the form of a colorless oil.

(b) Synthesis of 3-methyl-3-[3-(1-methylcyclohexyl)-4-methoxyphenyl]acrylonitrile:

4.5 g (18.3 mmol) of compound (a) were dissolved in 50 ml of THF and 3.2 g (27 mmol) of diethyl cyanomethylphosphonate and 2.4 g of ground potassium hydroxide were then successively added. The mixture was stirred at room temperature for four hours. The reaction medium was poured into ice-water and extracted with ethyl acetate, and the organic phase was separated out after settling of the phases had taken place, dried over magnesium sulfate and evaporated.

The residue obtained was purified by chromatography on a column of silica eluted with a mixture of dichloromethane and heptane (50/50); 2.86 g (58%) of the expected nitrile were collected.

(c) Synthesis of 3-[3-(1-methylcyclohexyl)-4-methoxyphenyl]crotonaldehyde:

2.8 g (10.4 mmol) of the above aldehyde were dissolved in 50 ml of anhydrous toluene, and 13 ml (13 mmol) of diisobutylaluminum hydride solution (1M in toluene) were added dropwise at –70° C. The mixture was permitted to return to 0° C. and was stirred for 30 minutes. Dilute hydrochloric acid was added slowly and the mixture was then filtered over Celite. The filtrate was washed with water, dried over magnesium sulfate and evaporated.

The residue obtained was purified by chromatography on a column of silica eluted with a mixture of dichloromethane and heptane (70/30). 2.34 g (83%) of the expected aldehyde were collected.

(d) Synthesis of ethyl trans-7-[3-(1-methylcyclohexyl)-4-hydroxyphenyl]-3,7-dimethyl-2,4,6-heptatrienoate:

In a manner similar to that of Example 5(d), by reaction of 2.3 g (8.6 mmol) of 3-[3-(1-methylcyclohexyl)-4-methoxyphenyl]crotonaldehyde with 4.4 ml (12.8 mmol) of triethyl 3-methyl-4-phosphono-2-butenoate, 2.13 g (65%) of the expected ethyl ester were obtained in the form of a yellow oil.

(e) Synthesis of trans-7-[3-(1-methylcyclohexyl)-4-hydroxyphenyl]-3,7-dimethyl-2,4,6-heptatrienoic acid:

In a manner similar to that of Example 1(e), starting with 2.13 g (5.5 mmol) of the above ethyl ester and after chromatography on a column of silica eluted with dichloromethane, 540 mg (27%) of trans-7-[3-(1-methylcyclohexyl)-4-hydroxyphenyl]-3,7-dimethyl-2,4,6-heptatrienoic acid, with a melting point of 175°–7° C., were obtained.

EXAMPLE 10

Preparation of (2Z,4E,6E)-7-[3-(1-methylcyclohexyl)-4-methoxyphenyl]-3,7-dimethyl-2,4,6-heptatrienoic acid In the reaction of Example 9(e), during the chromatography on a column of silica eluted with dichloromethane, 100 mg (5%) of (2Z,4E,6E)-7-[3-(1-methylcyclohexyl)-4-methylphenyl]-3,7-dimethyl-2,4,6-heptatrienoic acid, with a melting point of 165°–167° C., were also obtained.

EXAMPLE 11

Preparation of trans-7-[3-(1-adamantyl)-4-isopropyloxy-phenyl]-3,7-dimethyl-2,4,6-heptatrienoic acid (a) Synthesis of 3-(1-adamantyl)-4-isopropyloxyphenylethanone:

In a manner similar to that of Example 9(a), by reaction of 5 g (16 mmol) of 3-(1-adamantyl)-4-isopropyloxybenzoic acid with 25 ml (44 mmol) of methyllithium (1.6M), 4.9 g (98%) of the expected ketone derivative, with a melting point of 101°–2° C., were obtained.

(b) Synthesis of 3-methyl-3-[3-(1-adamantyl)-4-isopropyloxyphenyl]-acrylonitrile:

In a manner similar to that of Example 9(b), by reaction of 3.6 g (11.5 mmol) of the above ketone with 2.03 g (17.3 mmol) of diethyl cyanomethylphosphonate, 2.07 g (54%) of expected nitrile were obtained.

(c) Synthesis of 3-[3-(1-adamantyl)-4-isopropyloxyphenyl]crotonaldehyde:

In a manner similar to that of Example 9(c), starting with 3.1 g (9.2 mmol) of the above nitrile, 2.28 g (73%) of the expected aldehyde were obtained.

(d) Synthesis of ethyl trans-7-[3-(1-adamantyl)-4-isopropyloxyphenyl]-3,7-dimethyl-2,4,6-heptatrienoate:

In a manner similar to that of Example 5(d), by reaction of 1.37 g (4 mmol) of 3-[3-(1-adamantyl)-4-isopropyloxyphenyl]crotonaldehyde with 1.92 ml (6 mmol) of triethyl 3-methyl-4-phosphono-2-butenoate, 1 g (57%) of the expected ethyl ester were obtained in the form of a yellow oil.

(e) Synthesis of trans-7-[3-(1-adamantyl)-4-isopropyloxyphenyl]-3,7-dimethyl-2,4,6-heptatrienoic acid:

In a manner similar to that of Example 1(e), starting with 1.7 g (3.7 mmol) of the above ethyl ester and after chromatography on a column of silica eluted with dichloromethane, 800 mg (50%) of 7-[3-(1-adamantyl)-4-isopropyloxyphenyl]-3,7-dimethyl-2,4,6-heptatrienoic acid, with a melting point of 209°–10° C., were obtained.

EXAMPLE 12

Preparation of trans-7-[3-(1-adamantyl)-4-methoxypethoxy-methoxyphenyl]-3,7-dimethyl-2,4,6-heptatrienoic acid (a) Synthesis of 3-(1-adamantyl)-4-methoxyethoxymethoxphenylethanone:

In a manner similar to that of Example 9(a), by reaction of 17 g (47 mmol) of 3-(1-adamantyl)-4-methoxyethoxymethoxybenzoic acid with 73 ml (118 mmol) of methyllithium (1.6M), 18 g (100%) of the expected ketone derivative were obtained in the form of a yellow oil.

(b) Synthesis of 3-methyl-3-[3-(1-adamantyl)-4-methoxyethoxymethoxyphenyl]acrylonitrile:

In a manner similar to that of Example 9(b), by reaction of 5 g (14 mmol) of the above ketone with 3.4 ml (21 mmol) of diethyl cyanomethylphosphonate, 5.8 g (100% of expected nitrile were obtained in the form of a yellow oil.

(c) Synthesis of 3-[3-(1-adamantyl)-4-methoxyethoxymethoxyphenyl]-crotonaldehyde:

In a manner similar to that of Example 9(c), starting with 5.3 g (13.9 mmol) of the above nitrile, 2.4 g (100%) of the expected aldehyde, with a melting point of 80° C., were obtained.

(d) Synthesis of ethyl trans-7-[3-(1-adamantyl)-4-methoxyethoxy-methoxyphenyl]-3,7-dimethyl-2,4,6-heptatrienoate:

In a manner similar to that of Example 5(d), by reaction of 1.9 g (4.9 mmol) of 3-[3-(1-adamantyl)-4-methoxyethoxymethoxyphenyl]crotonaldehyde with 2 ml (7.3 mmol) of triethyl 3-methyl-4-phosphono-2-butenoate, 2 g (82%) of the expected ethyl ester, with a melting point of 83°–5° C., were obtained.

(e) Synthesis of trans-7-[3-(1-adamantyl)-4-methoxyethoxymethoxy-phenyl]-3,7-dimethyl-2,4,6-heptatrienoic acid:

In a manner similar to that of Example 1(e), starting with 2 g (4 mmol) of the above ethyl ester and after chromatography on a column of silica eluted with a mixture of ethyl acetate and dichloromethane (10/90), 710 mg (38%) of trans-7-[3-(1-adamantyl)-4-methoxyethoxymethoxyphenyl]-3,7-dimethyl-2,4,6-heptatrienoic acid, with a melting point of 170°–2° C., were obtained.

EXAMPLE 13

Preparation of ethyl trans-7-[3-(1-adamantyl)-4-methoxyphenyl]-7-methyl-2,4,6-heptatrienoate (a) Synthesis of 3-methyl-3-[3-(1-adamantyl)-4-methoxyphenyl]-acrylonitrile:

In a manner similar to that of Example 9(b), by reaction of 5 g (17.6 mmol) of 3-(1-adamantyl)-4-methoxyphenylethanone with 8.4 ml (52.8 mmol) of diethyl cyanomethylphosphonate, 3.8 g (70%) of expected nitrile, with a melting point of 163°–5° C., were obtained.

(b) Synthesis of 3-[3-(1-adamantyl)-4-methoxyphenyl] crotonaldehyde:

In a manner similar to that of Example 9(c), starting with 7 g (22.8 mmol) of the above nitrile, 4.8 g (68%) of the expected aldehyde, with a melting point of 163°–5° C., were obtained.

(c) Synthesis of ethyl trans-7-[3-(1-adamantyl)-4-methoxyphenyl]-7-methyl-2,4,6-heptatrienoate:

In a manner similar to that of Example 5(d), by reaction of 500 mg (1.6 mmol) of 3-[3-(1-adamantyl)-4-methoxyphenyl]crotonaldehyde with 550 µl (2.4 mmol) of triethyl trans-4-phosphono-2-butenoate, 540 mg (82%) of the expected ethyl ester, with a melting point of 143°–5° C., were obtained.

(d) Synthesis of trans-7-[3-(1-adamantyl)-4-methohxyphenyl]-7-methyl-2,4,6-heptatrienoic acid:

In a manner similar to that of Example 1(e), starting with 540 mg (1.3 mmol) of the above ethyl ester and after chromatography on a column of silica eluted with a mixture of ethyl acetate and dichloromethane (5/95), 220 mg (45%) of 7-[3-(1-adamantyl)-4-methoxyphenyl]-7-methyl-2,4,6-heptatrienoic acid were obtained.

EXAMPLE 14

Preparation of ethyl tran-7-(3-tert-butyl-4-methoxyethoxymethoxyphenyl)-3,7-dimethyl-2,4,6-heptatrienoate (a) Sinthesis of 3-tert-butyl-4-methoxyethoxymethoxyphenyl)-1-bromobenzene:

2.4 g (81 mmol) of sodium hydride (80% in oil) and 50 ml of DMF were introduced into a three-necked flask under a stream of nitrogen, and a solution of 17.6 g (77 mmol) of 2-tert-butyl-4-bromophenol in 100 ml of DMF was added dropwise and the mixture was stirred until the evolution of gas ceased. A solution of 10.5 ml (92 mmol) of 2-methoxyethoxymethyl chloride in 20 ml of DMF was then added dropwise and the mixture was stirred for four hours at room temperature. The reaction medium was poured into water and extracted with ethyl ether, and the organic phase was separated out after settling of the phases had taken place, washed with water, dried over magnesium sulfate and evaporated.

The residue was purified by chromatography on a column of silica eluted with a mixture of dichloromethane and hexane (50/50). After evaporation of the solvents, 21.4 g (88%) of the expected compound were collected in the form of a light brown oil.

(b) Synthesis of 3-tert-butyl-4-methoxyethoxymethoxybenzoic acid:

21.4 g (68 mmol) of the above compound were dissolved in 200 ml of THF, and a solution of 30 ml of n-butyllithium (2.5M in hexane) was added dropwise at −78° C. under a stream or nitrogen, and the mixture was stirred for 30 minutes. A stream of $CO_2$ was passed therethrough for one hour at −78° C. and the reaction medium was permitted to return to room temperature and poured into saturated aqueous ammonium chloride solution and extracted with ethyl ether, and the organic phase was separated out after settling of the phases had taken place, dried over magnesium sulfate and evaporated.

The residue obtained was purified by chromatography on a column of silica eluted with dichloromethane. 11 g (58%) of the expected acid were collected.

(c) Synthesis of 3-tert-butyl-4-methoxyethoxymethoxyphenylethanone:

In a manner similar to that of Example 9(a), by reaction of 11 g (39 mmol) of 3-tert-butyl-4-methoxyethoxymethoxybenzoic acid with 49 ml (78 mmol) of methyllithium (1.6M), 8.5 g (75%) of the expected ketone derivative were obtained in the form of yellow oil.

(d) Synthesis of 3-methyl-(3-tert-butyl-4-methoxyethoxymethoxyphenyl)acrylonitrile:

In a manner similar to that of Example 9(b), by reaction of 8.5 g (30 mmol) of the above ketone with 14.3 ml (90 mmol) of diethyl cyanomethylphosphonate, 7 g (76%) of expected nitrile were obtained in the form of a yellow oil.

(e) Synthesis of 3-(3-tert-butyl-4-methoxyethoxymethocyphenyl)-crotonaldehyde:

In a manner similar to that of Example 9(c), starting with 7 g (23 mmol) of the above nitrile, 6 g (85%) of the expected aldehyde were obtained in the form of a yellow oil.

(f) Synthesis of ethly trans-7-(3-tert-butyl-4-methoxyethoxymethoxyphenyl )-3,7-dimethyl-2,4,6-heptatrienoate:

In a manner similar to that of Example 5(d), by reaction of 6 g (19.6 mmol) of 3-(3-tert-butyl-4- methoxyethoxymethoxyphenyl)crotonaldehyde with 8.1 ml (29.4 mmol) of triethyl 3-methyl-4-phosphono-2-butenoate, 6.6 g (81%) of the expected ethyl ester were obtained in the form of a yellow oil.

(g) Synthesis of trans-7-(3-tert-butyl-4-methoxyethoxymethoxyphenyl)-3,7-dimethyl-2,4,6-heptatrienoic acid:

In a manner similar to that of Example 1(e), starting with 1.1 g (2.6 mmol) of the above ethyl ester and after recrystallization in a mixture of dichloromethane and heptane, 320 mg (32%) of trans-7-(3-tert-butyl-4-methoxyethoxymethoxyphenyl)-3,7-dimethyl -2,4,6-heptatrienoic acid, with a melting point of 147°–8° C., were obtained.

EXAMPLE 15

In this example, various specific formulations based on the compounds according to the invention are illustrated.

(A) ORAL ROUTE:

(a) 0.2 g Tablet:

| | | |
|---|---|---|
| (i) | Compound prepared in Example 3 | 0.001 g |
| (ii) | Starch | 0.114 g |
| (iii) | Dicalcium phosphate | 0.020 g |
| (iv) | Silica | 0.020 g |
| (v) | Lactose | 0.030 g |
| (vi) | Talc | 0.010 g |
| (vii) | Magnesium stearate | 0.005 g |

(b) Oral (drinkable) suspension in 10 ml ampoules:

| | | |
|---|---|---|
| (i) | Compound of Example 3 | 0.05 g |
| (ii) | Glycerol | 1.000 g |
| (iii) | 70% Sorbitol | 1.000 g |
| (iv) | Sodium saccharinate | 0.010 g |
| (v) | Methyl para-hydroxybenzoate | 0.080 g |
| (vi) | Flavoring | qs |
| (vii) | Purified water | qs 10 ml |

(B) TOPICAL ROUTE:

(a) Ointment:

| | | |
|---|---|---|
| (i) | Compound of Example 3 | 0.020 g |
| (ii) | Isopropyl myristate | 81.700 g |
| (iii) | Liquid petrolatum | 9.100 g |
| (iv) | Silica ("Aerosil 200" marketed by Degussa) | 9.180 g |

(b) Ointment:

| | | |
|---|---|---|
| (i) | Compound of Example 3 | 0.300 g |
| (ii) | White petrolatum codex | qs 100 g |

(c) Nonionic water-in-oil cream:

| | | |
|---|---|---|
| (i) | Compound of Example 3 | 0.100 g |
| (ii) | Mixture of oils, waxes and emulsified lanolin alcohols ("Anhydrous Eucerine" marketed by BDF) | 39.900 g |
| (iii) | Methyl para-hydroxybenzoate | 0.075 g |
| (iv) | Propyl para-hydroxybenzoate | 0.075 g |
| (v) | Sterile demineralized water | qs 100 g |

(d) Lotion:

| | | |
|---|---|---|
| (i) | Compound of Example 3 | 0.100 g |
| (ii) | Polyethylene glycol (PEG 400) | 69.900 g |
| (iii) | 95% Ethanol | 30.000 g |

(e) Hydrophobic ointment:

| | | |
|---|---|---|
| (i) | Compound of Example 3 | 0.300 g |
| (ii) | Isopropyl myristate | 36.400 g |
| (iii) | Silicone oil ("Rhodorsil 47 V 300" marketed by Rhone-Poulenc) | 36.400 g |
| (iv) | Beeswax | 13.600 g |

| | | |
|---|---|---|
| (v) | Silicone oil ("Abil 300,000 cst" marketed by Goldschmidt) | qs 100 g |

(f) Nonionic oil-in-water cream:

| | | |
|---|---|---|
| (i) | Compound of Example 3 | 0.500 g |
| (ii) | Cetyl alcohol | 4.000 g |
| (iii) | Glyceryl monostearate | 2.500 g |
| (iv) | PEG 50 stearate | 2.500 g |
| (v) | Karite butter | 9.200 g |
| (vi) | Propylene glycol | 2.000 g |
| (vii) | Methyl para-hydroxybenzoate | 0.075 g |
| (viii) | Propyl para-hydroxybenzoate | 0.075 g |
| (ix) | Sterile demineralized water | qs 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An aromatic polenic compound having the structural formula (I):

$$\text{(structure with substituents } R_1, R_2, R_3, R_4, R_5, R_6, R_7, R_8 \text{)} \quad (I)$$

in which $R_1$ is a —$CH_3$ radical, a radical —$CH_2$—O—$R_9$, a radical —$CH_2$—O—CO—$R_{10}$, or a radical —CO—$R_{11}$, wherein $R_9$, $R_{10}$, and $R_{11}$ are as defined below; $R_2$ is a hydrogen atom or a lower alkyl radical having 1 to 6 carbon atoms; $R_3$ is a hydrogen atom or a lower alkyl radical having 1 to 6 carbon atoms; $R_5$ is a hydrogen atom or a lower alkyl radical having 1 to 6 carbon atoms; $R_7$ and $R_8$ independently are each (i) a hydrogen atom, (ii) a linear or branched alkyl radical having from 1 to 20 carbon atoms, (iii) a cycloaliphatic radical selected from the group consisting of 1-methylcyclohexyl and 1-adamantyl, (iv) a radical —O—$CH_2$—O—$CH_2$—$CH_2$—O—$CH_3$, (v) a radical —O—$R_{13}$, or (vi) a radical —S(O)$_n R_{13}$, wherein $R_{13}$ and n are as defined below, $R_4$ and $R_6$ together form, with the carbon atoms from which they depend and with the adjacent benzene ring, a naphthalene ring, and at least one of $R_7$ and $R_8$ has the above definition (ii) or (iii); $R_9$ is a hydrogen atom or a lower alkyl radical having 1 to 6 carbon atoms; $R_{10}$ is a lower alkyl radical having 1 to 6 carbon atoms; $R_{11}$ is (a) a hydrogen atom, (b) a lower alkyl radical having 1 to 6 carbon atoms, (c) a radical of formula:

$$\diagdown N \diagup \atop | \atop R''^{R'}$$

in which R' and R" independently are each a hydrogen atom, a lower alkyl radical having 1 to 6 carbon atoms, a mono- or polyhydroxyalkyl radical respectively having 2 to 3 carbon atoms or 3 to 6 carbon atoms containing 2 to 5 hydroxyl groups, or an optionally substituted phenyl radical which if substituted, is substituted with at least one halogen atom, hydroxyl or nitro group, or (d) a radical —$OR_{12}$, wherein $R_{12}$ is a hydrogen atom, a linear or branched alkyl radical having from 1 to 20 carbon atoms, an alkenyl radical having 2 to 5 carbon atoms and at least one site of ethylenic

19 unsaturation, a mono- or poly-hydroxyalkyl radical respectively having 2 to 3 carbon atoms or 3 to 6 carbon atoms and 2 to 5 hydroxyl groups, or an optionally substituted phenyl or radical benzyl or pheneyl radical wherein, if substituted, are substituted by at least one halogen atom, hydroxyl or nitro functional group; $R_{13}$ is a hydrogen atom or a linear or branched alkyl radical having from 1 to 20 carbon atoms; and n is an integer equal to 0, 1 or 2; or a pharmaceutically/cosmetically acceptable salt or optical or geometric isomer thereof.

2. An aromatic polyenic compound as defined by claim 1, comprising a pharmaceutically acceptable salt thereof.

3. An aromatic polyenic compound as defined by claim 1, wherein formula (I), the lower alkyl radical substituents are selected from the group consisting of methyl, ethyl, isopropyl, butyl, tert-butyl and hexyl radicals.

4. An aromatic polyenic compound as defined by claim 1, wherein formula (I), the linear or branched alkyl radical substituents having from 1 to 20 carbon atoms are selected from the group consisting of methyl, ethyl, propyl, 2-ethylhexyl, octyl, dodecyl, hexadecyl and octadecyl radicals.

5. An aromatic polyenic compound as defined by claim 1, wherein formula (I), the monohydroxyalkyl radical substituents are selected from the group consisting of 2-hydroxypropyl and 3-hydroxypropyl radicals.

6. An aromatic polyenic compound as defined by claim 1, wherein formula (I), the polyhydroxyalkyl radical substituents are selected from the group consisting of 2,3-dihydroxypropyl, 2,3,4-trihydroxybutyl, 2,3,4,5-tetrahydroxypentyl and pentaerythritol radicals.

7. An aromatic polyenic compound selected from the group consisting of trans-7-[3-(1-adamantyl)-4-hydroxyphenyl]-3,7-dimethyl-2,4,6-heptatrienoic acid; ethyl trans-7-[3-(1-adamantyl)-4-methoxyphenyl]-3,7-dimethyl-2,4,6-heptatrienoate; trans-7-[-3-(1-adamantyl)-4-methoxyphenyl]-3,7-dimethyl-2,4,6-heptatrienoic acid; (2Z, 4E,6E)-7-[3-(1-adamantyl)-4-methoxyphenyl]-3,7-dimethyl-2,4,6-heptatrienoic acid; trans-5-[-7-(1-adamantyl)-6-methoxyethoxymethoxy-2-naphthyl]-3-methyl-2,4,-pentadienoic acid; trans-5-[-7-(1-adamantyl)-6-hydroxy-2-naphthyl]-3-methyl-2,4-pentadienoic acid; trans-5-[-7-(1-adamantyl)-6-methoxy-2-naphthyl]-3-methyl-2,4-pentadienoic acid; trans-5-[-7-(1-adamantyl)-6-propyloxy-2-naphthyl]-3-methyl-2,4-pentadienoic acid; trans-7-[3-(1-methylcyclohexyl)-4-hydroxy-phenyl]-3,7-dimethyl]-2,4,6-heptatrienoic acid; (2Z,4E,6E)-7-[3-(1-methylcyclohexyl)-4-methoxyphenyl]-3,7-dimethyl-2,4,6-heptatrienoic acid; trans-7-[3-(1-adamantyl)-4-isopropyloxy-phenyl]-3,7-dimethyl-2,4,6-heptatrienoic acid; trans-7-[3-(1-adamantyl)-4-methoxyethoxymethoxyphenyl]-3,7-dimethyl-2,4,6-heptatrienoic acid; trans-7-[3-(1-adamantyl)-4-methoxyphenyl]-7-methyl-2,4,6-heptatrienoic acid; trans-7-[3-(1-adamantyl)-4-methoxyphenyl]-3,7-dimethyl-2,4,6-heptatrien-1-ol; trans-7-[3-(1-adamantyl)-4-methoxyphenyl]-3,7-dimethyl-2,4,6-heptatrien-1-al; trans-N-ethyl-7-[3-(1-adamantyl)-4-methoxy-phenyl]-3,7-dimethyl-2,4,6-heptatrienecarboxamide; trans-N-4-hydroxyphenyl-7-[3-(1-adamantyl)-4-methoxyphenyl]-3,7-dimethyl-2,4,6-heptatrienecarboxamide; trans-7-(3-tert-butyl-4-methoxyethoxymethoxy-phenyl)-3,7-dimethyl-2,4,6-heptatrienoic acid; ethyl trans-7-(3-tert-butyl-4-hydroxyphenyl)-3,7-dimethyl-2,4,6-heptatrienoate; ethyl trans-7-(3-tert-butyl-4-methoxyphenyl)-3,7-dimethyl-2,4,6-heptatrienoate; and ethyl trans-7-[4-(1-adamantyl)-3-methoxyphenyl]-3,7-dimethyl-2,4,6-heptatrienoate.

8. An aromatic polyenic compound as defined by claim 2, which is an alkali or alkaline earth metal, zinc or amine salt.

9. An aromatic polyenic compound as defined by claim 1, wherein formula (I), at least one of the following definitions exist:

$R_1$ is a radical —CO—$R_{11}$; or $R_7$ is the adamantyl radical.

10. A pharmaceutical composition of matter, comprising a therapeutically effective amount of an aromatic polyenic compound as defined by claim 1, or pharmaceutically acceptable salt or isomer thereof, and a pharmaceutically acceptable vehicle, carrier or diluent therefor.

11. The pharmaceutical composition as defined by claim 10, further comprising a retinoid compound, a D vitamin, a corticosteroid, an anti-free radical agent, an α-hydroxy or α-keto acid an ion channel blocker, or combination thereof.

12. The pharmaceutical composition as defined by claim 10, selected from the group consisting of a tablet, a capsule, a syrup, a dragee, a suspension, an elixir, a solution, a powder, granules, an emulsion, microspheres, nanospheres, lipid vesicles, polymeric vesicles, and a composition for injection.

13. The pharmaceutical composition as defined by claim 10, selected from the group consisting of an ointment, a cream, a milk, a salve, an impregnated pad, a gel, a spray, or a lotion.

14. The pharmaceutical composition as defined by claim 10, for topical administration.

15. The pharmaceutical composition as defined by claim 10, for systemic administration.

16. The pharmaceutical composition as defined by claim 10, comprising from 0.001% to 5% by weight of said aromatic polyenic compound, or salt or isomer thereof.

17. A cosmetic composition of matter, comprising a cosmetically effective amount of an aromatic polyenic compound as defined by claim 1, or cosmetically acceptable salt or isomer thereof, and a cosmetically acceptable vehicle, carrier or diluent therefor.

18. The cosmetic composition as defined by claim 17, which is selected from the group consisting of a cream, a milk, a lotion, a gel, an ointment, microspheres, nanospheres, lipid vesicles, polymeric vesicles, a soap, and a shampoo.

19. The cosmetic composition as defined by claim 17, comprising from 0.001% to 3% by weight of said aromatic polyenic compound, or salt or isomer thereof.

20. The cosmetic composition as defined by claim 17, further comprising a compound selected from the group consisting of retinoid compound, a D vitamin a corticosteroid, an anti-free radical agent, an α-hydroxy or α-keto acid an ion channel blocker, and combinations thereof.

21. The pharmaceutical composition as defined by claim 10, further comprising a compound selected from the group consisting of a wetting agent, a depigmenting agent, a moisturizing agent, an emollient, an antiseborrhoeic or anti-acne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, and combinations thereof.

22. The pharmaceutical composition as defined by claim 10, further comprising a compound selected from the group consisting of a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, and combinations thereof.

23. The cosmetic composition by claim 17, further comprising a compound selected from the group consisting of a wetting agent, a depigmenting agent, a moisturizing agent, an emollient, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, and combinations thereof.

24. The cosmetic composition as defined by claim 17 further comprising a compound selected from the group consisting of a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, and combinations thereof.

* * * * *